United States Patent
Podrebarac

(10) Patent No.: US 7,154,013 B2
(45) Date of Patent: Dec. 26, 2006

(54) OLEFIN METATHESIS

(75) Inventor: Gary G. Podrebarac, Nassau Bay, TX (US)

(73) Assignee: Catalytic Distillation Technologies, Pasadena, TX (US)

(*) Notice: Subject to any disclaimer, the term of this patent is extended or adjusted under 35 U.S.C. 154(b) by 470 days.

(21) Appl. No.: 10/431,101

(22) Filed: May 7, 2003

(65) Prior Publication Data

US 2003/0204123 A1    Oct. 30, 2003

Related U.S. Application Data

(62) Division of application No. 09/035,174, filed on Mar. 4, 1998, now Pat. No. 6,583,329.

(51) Int. Cl.
  *C07C 6/04* (2006.01)
  *C07C 6/02* (2006.01)
(52) U.S. Cl. .................. 585/326; 585/643; 585/329; 203/DIG. 6
(58) Field of Classification Search .............. 585/326, 585/324, 643; 203/DIG. 6
  See application file for complete search history.

(56) References Cited

U.S. PATENT DOCUMENTS

| | | | |
|---|---|---|---|
| 3,697,613 A | 10/1972 | Arganbright | 260/683 |
| 3,702,827 A | 11/1972 | Arganbright | 252/441 |
| 3,792,108 A | 2/1974 | Arganbright | 260/683 |
| 3,923,920 A | 12/1975 | Regien | 260/683 |
| 4,709,115 A | 11/1987 | Jung et al. | 585/643 |
| 5,026,936 A | 6/1991 | Leyshon et al. | 585/315 |
| 5,235,102 A | 8/1993 | Palmer et al. | 562/607 |
| 5,449,852 A | 9/1995 | Chauvin et al. | 585/647 |
| 5,596,115 A | 1/1997 | Commereuc | 556/27 |

FOREIGN PATENT DOCUMENTS

| | | |
|---|---|---|
| EP | 0304515 A1 | 1/1989 |
| EP | 0664776 B1 | 2/1995 |

*Primary Examiner*—Thuan D Dang
(74) *Attorney, Agent, or Firm*—Kenneth H. Johnson

(57) ABSTRACT

A process in which tetramethylethylene and neohexene are produced by starting with butene in a distillation column reactor to produce a product containing ethylene, diisobutene, tetramethylethylene, heavier oligomers. After separating these components, the separated diisobutene is further reacted with ethylene produced from the first step to produce neohexene.

2 Claims, 5 Drawing Sheets

OLEFIN METATHESIS

This application is a DIV of application Ser. No. 09/035,174, filed Mar. 4, 1998, now U.S. Pat. No. 6,583,329.

BACKGROUND OF THE INVENTION

1. Field of the Invention

The present invention relates to a process for the metathesis of olefins. More particularly the invention relates to a process wherein the catalyst is part of a distillation structure and the products are simultaneously separated from the reactants and each other by fractional distillation during the reaction.

2. Related Art

Broadly metathesis has been defined as a chemical reaction in which an element or radical in one compound changes places with another element or radical in another compound. See *The Van Nostrand Chemist's Dictionary*, D. Van Nostrand Company, Inc., 1953, page 463. More specifically olefin metathesis can be defined as the redistribution of alkylidene moieties to give a mixture of olefins. In effect, this reaction takes place via cleavage of the olefin double bond. Generally the reactions of olefinic molecules in the presence of metal-containing catalysts to produce other olefinic molecules are known in the art as "disproportionation", "dismutation" or "metathesis" reactions.

The metathesis reactions are of considerable interest because of the versatility of the reaction and the numerous olefinic hydrocarbons available from petrochemical sources which are suitable for use in the reaction to yield useful products. One such reaction is the metathesis of propylene with itself to produce n-butene and ethylene. See, for example, U.S. Pat. No. 4,046,832. The reverse reaction is the metathesis of ethylene with n-butene to produce propylene and is disclosed in U.S. Pat. No. 5,026,936. Another use of the metathesis reaction is to produce 2-methyl-2-butene from the reaction of 2-methyl-1-propene and 2-butene. See U.S. Pat. No. 3,702,827.

Finally, the simultaneous disproportionation of olefins and fractional distillation is reported in U.S. Pat. No. 4,709,115. Therein the disproportionation of butene with itself to produce ethylene or propylene and hexene or pentenes is disclosed.

Catalysts that are known to catalyze the metathesis include the oxides of tungsten, rhenium and cobalt/molybdenum.

SUMMARY OF THE INVENTION

Briefly the present invention relates to metathesis reaction carried out a in distillation column reactor, that is, reaction and fractional distillation of the reactants and products are carried out concurrently in the distillation column reactor wherein the catalyst may be in the form to act as a distillation structure or part of a distillation structure or alternatively the catalyst may be located in beds or zones preferably located within the distillation column reactor.

One embodiment of the present invention comprises the production of propylene from the reaction of 2-butene with ethylene in a distillation column reactor. Preferably the catalyst is supplied in the form to act as a distillation structure or part of a distillation structure and loaded into the upper portion of a distillation column reactor. The 2-butene is fed above the bed and the ethylene is fed below the bed. Product propylene is taken as overhead and any heavies produced are removed as bottoms.

In a second embodiment the present invention relates to a process for the production of higher molecular weight olefins useful in the manufacture of detergents. More particularly the invention relates to the metathesis of olefins having higher molecular weight than that desired with lower molecular olefins to produce the desired molecular weight olefins.

In another embodiment the present invention comprises the metathesis of isobutylene with 2-butene to produce 2-methyl-2-butene and propylene. The catalyst is loaded into the upper portion of a distillation column reactor. The isobutylene is fed below the bed. Product 2-methyl-2-butene is taken as bottoms while propylene is removed as overheads.

Another embodiment of the present invention comprises the metathesis of isobutylene with itself to produce 2,3-dimethyl-2-butene (tetramethylethylene or TME) and ethylene. The catalyst is loaded into the upper portion of a distillation column reactor. The isobutylene is fed below the bed. Product TME is taken as bottoms along with any $C_8=$ or $C_{12}=$ oligomerization product. Ethylene is removed as overheads. The TME is separated from the heavy oligomers by fractional distillation. The $C_8=$ oligomers are then separated from the $C_{12}=$ oligomers by fractional distillation and fed to a single pass down flow reactor with ethylene for metathesis to 3,3-dimethyl-1-butene (neohexene).

DETAILED DESCRIPTION OF THE INVENTION

Figure 1:
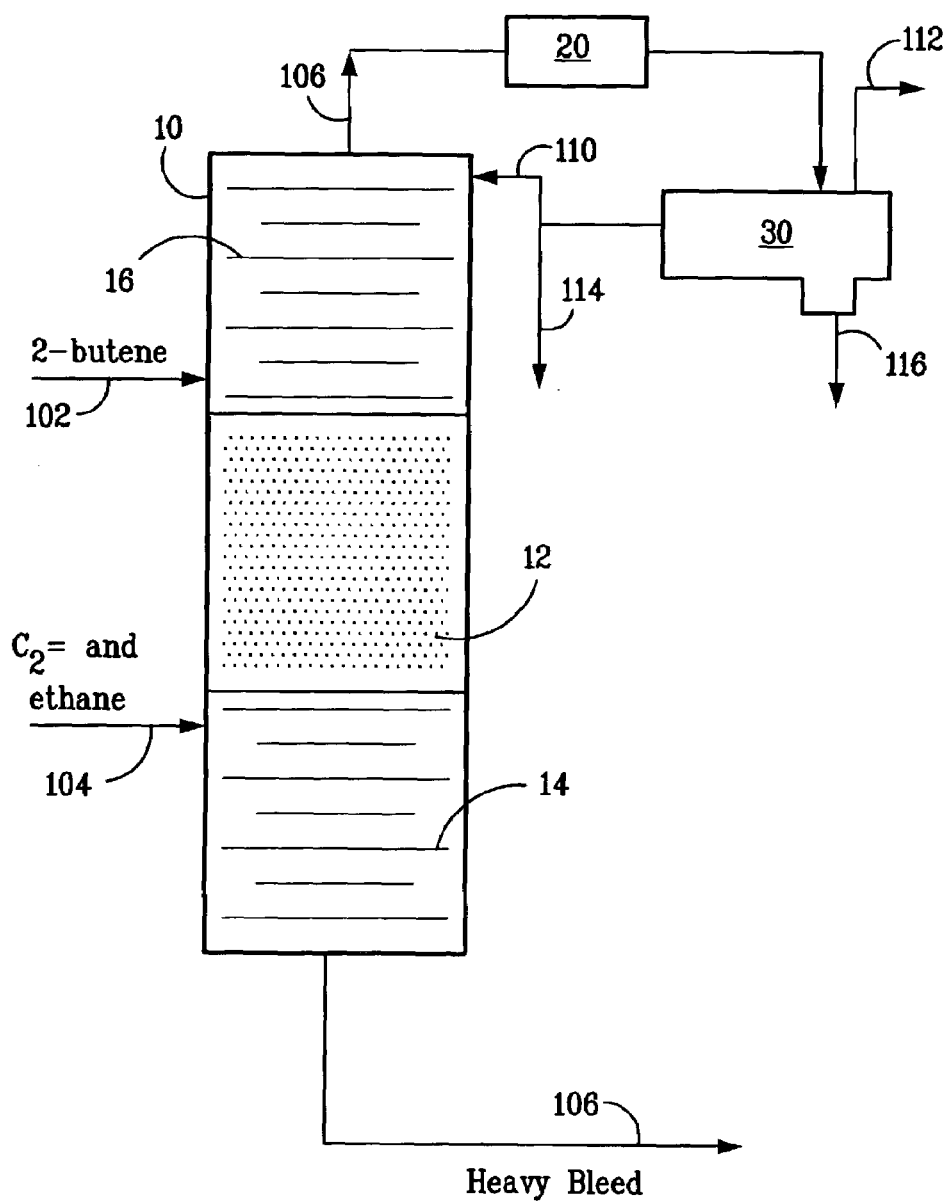
FIG. 1 is schematic flow diagram of an embodiment that demonstrates the use of catalytic distillation to produce propylene from the metathesis of ethylene and 2-butene.

The reactions are preferably carried out under conditions of catalytic distillation. In a catalytic distillation, i.e., the catalyst serves as a distillation component The catalytic material is preferably a component of a distillation system functioning as both a catalyst and distillation packing, i.e., a packing for a distillation column having both a distillation function and a catalytic function: for example, rings, saddles, balls, irregular, sheets, tubes, spirals, packed in bags (as described in U.S. Pat. No. 4,242,530), plated on grills or screens, reticulated polymer foams (the cellular structure of the foams must be sufficiently large so as not to cause high pressure drops through the column or otherwise arranged, such as in chunks or concentration tubes to allow vapor flow) or honeycomb monoliths. The reaction system can be described as heterogenous since the catalyst remains a distinct entity.

A preferred catalyst structure for use in the distillation column reactors for the present hydrogenations comprises flexible, semi-rigid open mesh tubular material, such as stainless steel wire mesh, filled with a particulate catalytic material One new catalyst structure developed for use in hydrogenations is described in U.S. Pat. No. 5,266,546 which is incorporated herein in its entirety. Another catalyst structure particularly suited for hydrogenations is described in U.S. Pat. No. 5,431,890 which is incorporated herein in its entirety.

U.S. Pat. Nos. 4,242,530 and 4,443,559 which are incorporated herein, disclose particulate catalyst in a plurality of pockets in a cloth belt or wire mesh tubular structures, which is supported in the distillation column reactor by open mesh knitted stainless steel wire by twisting the two together into a helix. U.S. Pat. No. 5,348,710, which is incorporated herein, describes several other suitable structures in the prior art and discloses new structures suitable for this process.

Other catalytic distillation structures useful for this purpose are disclosed in U.S. Pat. Nos. 4,731,229 and 5,073,236 which are also incorporated by reference.

In addition to the catalytic systems described above, reactive distillation systems such as those disclosed in U.S. Pat. Nos. 4,536,373, 4,774,364, 4,847,430 and 5,510,089, which are incorporated herein, may be used to carry out the present process.

The particulate catalyst material may be a powder, small irregular chunks or fragments, small beads and the like. The particular form of the catalytic material in the cloth pockets is not critical, so long as sufficient surface area is provided to allow a reasonable reaction rate. The sizing of catalyst particles can be best determined for each catalytic material (since the porosity or available internal surface area will vary for different material and of course affect the activity of the catalytic material).

The distillation column reactor can be appreciated to contain a vapor phase and some liquid phase as in any distillation. The success of the concurrent distillation and reaction approach lies in an understanding of the principles associated with distillation. First, because the reaction is occurring concurrently with distillation, the initial reaction products are removed from the reaction zone as quickly as possible. Second, because all the components are boiling the temperature of reaction is controlled by the boiling point of the mixture at the system pressure. The heat of reaction simply creates more boil up, but no increase in temperature. Third, the reaction has an increased driving force because the reaction products have been removed and cannot contribute to a reverse reaction (LeChatelier's Principle).

As a result, a great deal of control over the rate of reaction and distribution of products can be achieved by regulating the system pressure. Also, adjusting the throughput (residence time=liquid hourly space velocity$^{-1}$) gives further control of product distribution and degree of conversion to metathesis product.

The temperature in a distillation column reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus effected by a change in pressure; by increasing the pressure, the temperature in the system is increased, and vice versa.

A reflux is preferably included in the system. The reflux ratio could vary over the rate 0.5:1 to 33:1. In practice, the higher ratio may be used to compensate for a short catalyst bed such as required for experimental work. In commercial size units the catalyst bed would be provided so that lower reflux and hence higher unit productivity could be obtained at lower operating cost.

Suitable catalysts for the metathesis are the supported oxides of cobalt, molybdenum, rhenium or mixtures of cobalt and molybdenum oxides. Either silica or alumina based supports for the oxides may be used. The distillation column reactor is generally operated at an overhead pressure to result in a catalyst bed temperature of 100–200° C. for $CoOMoO_3$ catalyst and about room temperature for the $Re_2O_7$ catalyst bearing in mind the effect of pressure on temperature as discussed above.

The specific metathesis reactions of interest are:

I. Propylene Process

The reaction of 2-butene with ethylene to produce propylene because of the availability of the 2-butene and the value of propylene. The 2-butene can be produced from the dimerization of ethylene. The reaction is reversible in fixed bed reactors for a given residence time and may be written as follows:

In a distillation column reactor, the equilibrium is constantly disturbed, thus although the equilibrium concentration of propylene at a given temperature is rather low, the removal of the propylene as an overhead product constantly drives the reaction to increase production of propylene. Adjusting the throughput gives further control of product distribution and degree of conversion to propylene. The production of undesirable side products, i.e., the isomerization of 2-butene to 1-butene, followed by their metathesis to pentenes and hexenes, is prevented or minimized.

Another advantage of the catalytic distillation reactor is that the feeds will be dried by azeotropic distillation allowing long periods of catalytic activity without the special drying steps that would otherwise be necessary. The necessity for dry feed is indicated in U.S. Pat. No. 3,340,322 where the dried feed is specified for the examples.

Referring now to the FIG. 1 a simplified flow diagram of the propylene process may be seen. The reaction distillation column 10 is seen to contain a bed 12 of the catalyst in the upper portion of the column. Below the catalyst bed 12 is a stripping section 14 containing standard distillation structure such as sieve trays, bubble cap trays or inert packing. Above the catalyst bed 12 is a rectification section 16 also containing standard distillation structure.

The 2-butene feed in liquid form is fed above the catalyst via flow line 102 and the ethylene is fed as gas below the catalyst bed via flow line 104. The ethylene flows upward into the bed 12 and reacts to form propylene which is removed as overheads via flow line 106 along with the small amount of unreacted ethylene. The column is operated to keep the 2-butene concentrated within the catalyst bed by internal reflux with feed being added as necessary to make up that reacted. The rectification section 16 insures that the 2-butene is separated from the $C_3$ and lighter material (propylene product and unreacted ethylene). The 2-butene is present in large excess to the ethylene, i.e. 25 moles 2-butene to 1 mole ethylene. A bottoms draw via flow line 108 is taken to remove any heavier by products produced in the reactor.

The overheads in flow line 106 is cooled in condenser 20 and the liquid collected in receiver/separator 30. A portion of the liquid product may be returned to the distillation column reactor 10 as reflux via flow line 110. Product propylene can be removed as a gas via flow line 112 or liquid via flow line 114.

If desirable the ethylene feed may be contained in a mixed ethane/ethylene stream in which case the ethane would be removed as overheads along with the propylene and unreacted ethylene. The ethane and unreacted ethylene could then be separated in receiver separator 30 and removed via flow line 112 with the product propylene being removed via flow line 114. Any water is removed overhead as an azeotrope and phases out in receiver/separator 30 from which it is recovered via line 116.

II. Higher Olefin Process

The specific metathesis reaction of interest is the reaction of higher molecular olefins ($C_{15}+$) with $C_3$–$C_8$ olefins to produce detergent range olefins ($C_{10}$–$C_{14}$). Conversion is limited by equilibrium in fixed bed straight pass reactors. In a catalytic distillation, i.e., the catalyst may serve as a distillation component, the equilibrium is constantly disturbed, thus although the equilibrium concentration of the detergent range olefins at a given temperature is rather low, the removal of the product as bottoms product constantly drives the reaction to increase production of the desired olefins.

Figure 2:
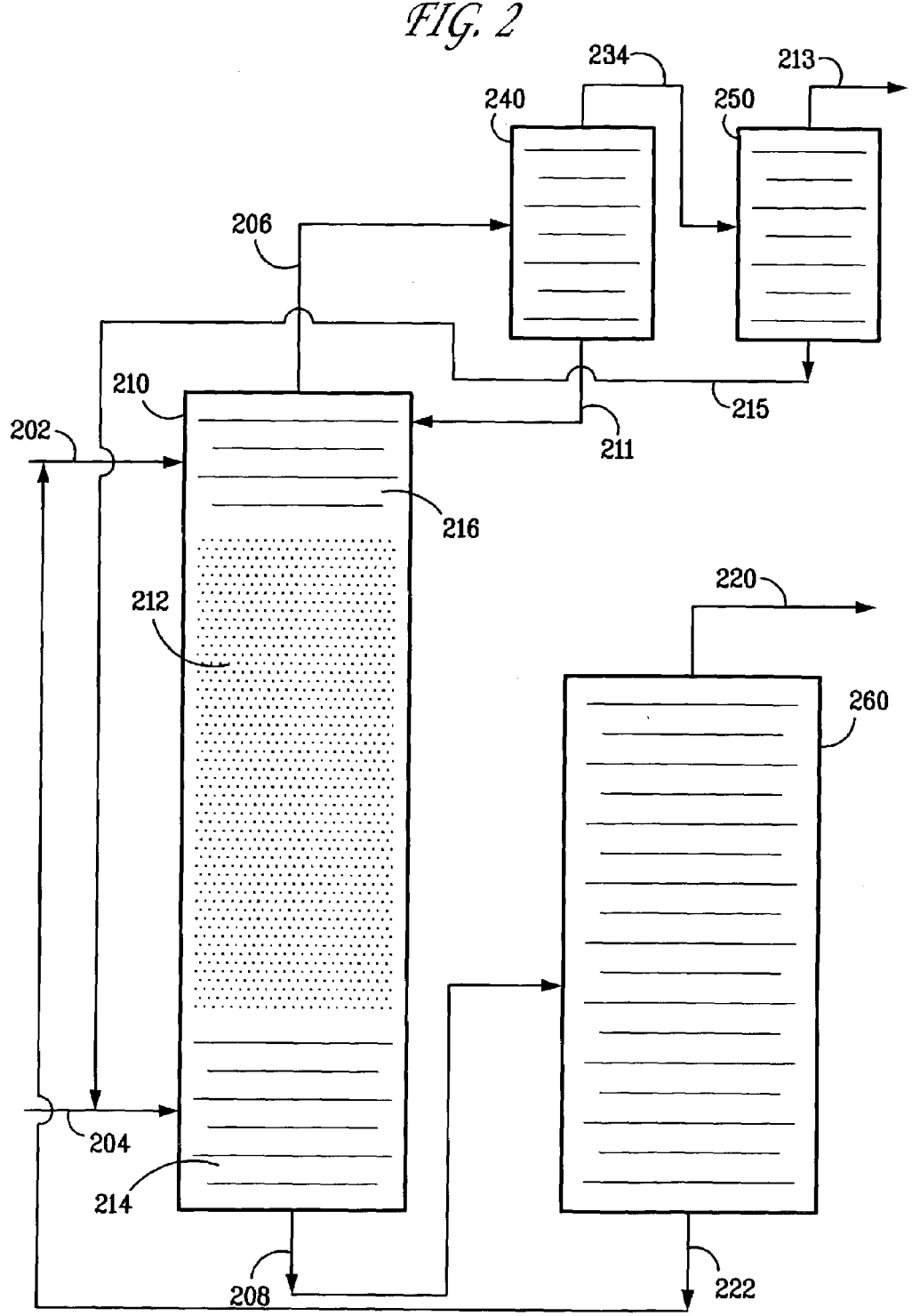
FIG. 2 is a schematic flow diagram of an embodiment for the production of higher olefins.

Referring now to FIG. 2 a simplified flow diagram of the process may be seen. The reaction distillation column 210 is seen to contain a bed 212 of the catalyst in the upper portion of the column. Below the catalyst bed 212 is a stripping section 214 containing standard distillation structure such as sieve trays, bubble cap trays or inert packing. Above the catalyst bed 212 is a rectification section 216 also containing standard distillation structure.

The heavy olefin feed is fed above the catalyst bed in liquid form via flow line 202 and the light olefins are fed below the catalyst bed via flow line 204. The light olefins flow upward into the bed 212 and react with the heavy olefins to form the desired detergent range olefins which are removed as bottoms via flow line 208 along with the unreacted heavier olefins. The bottoms from the distillation column reactor are fed via flow line 208 to bottoms splitter 260 where the detergent range olefins are taken as overheads via flow line 220. The heavier olefins are removed from splitter 260 as bottoms via flow line 222 and are recycled back to the feed in flow line 202.

The column is operated to keep the $C_5$–$C_8$ olefins concentrated within the catalyst bed by internal reflux with feed being added as necessary to make up that reacted. The rectification section 216 insures that these olefins are refluxed within the column. Unreacted lighter olefins and any light olefins produced by the reaction are removed as overheads via flow line 206.

The overheads are passed first to a debutanizer column 240 where the $C_4$ and lighter components are removed as overheads. The bottoms, consisting mostly of $C_5$–$C_8$ olefins are recycled to the distillation column reactor as external reflux via flow 211. The $C_4$ and lighter olefins from the debutanizer are fed to a deethanizer 250 wherein the $C_2$ and lighter olefins and any water in the feed are taken as overheads via flow line 213 to be recycled to an oligomerization unit to produce more heavy olefins. The $C_3$ and $C_4$ olefins are removed as bottoms via flow line 215 and recycled with the light olefin feed in flow line 204.

III. 2MB2 and Propylene

The specific metathesis reaction of interest is the metathesis of isobutylene with 2-butene to produce 2-methyl-2-butene and propylene. The reaction is reversible in fixed bed straight pass reactors for a given residence time. The reaction may be written as follows:

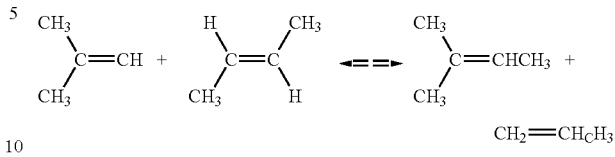

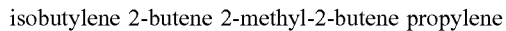

isobutylene 2-butene 2-methyl-2-butene propylene

The 2-methyl-2-butene product is useful as a precursor for the production of isoprene. Propylene is also a useful olefin for polymer production.

In a catalytic distillation, i.e., the catalyst serves as a distillation component, the equilibrium is constantly disturbed, thus although the equilibrium concentration of propylene at a given temperature is rather low, the removal of the propylene as an overhead product constantly drives the reaction to increase production of propylene.

Figure 3:
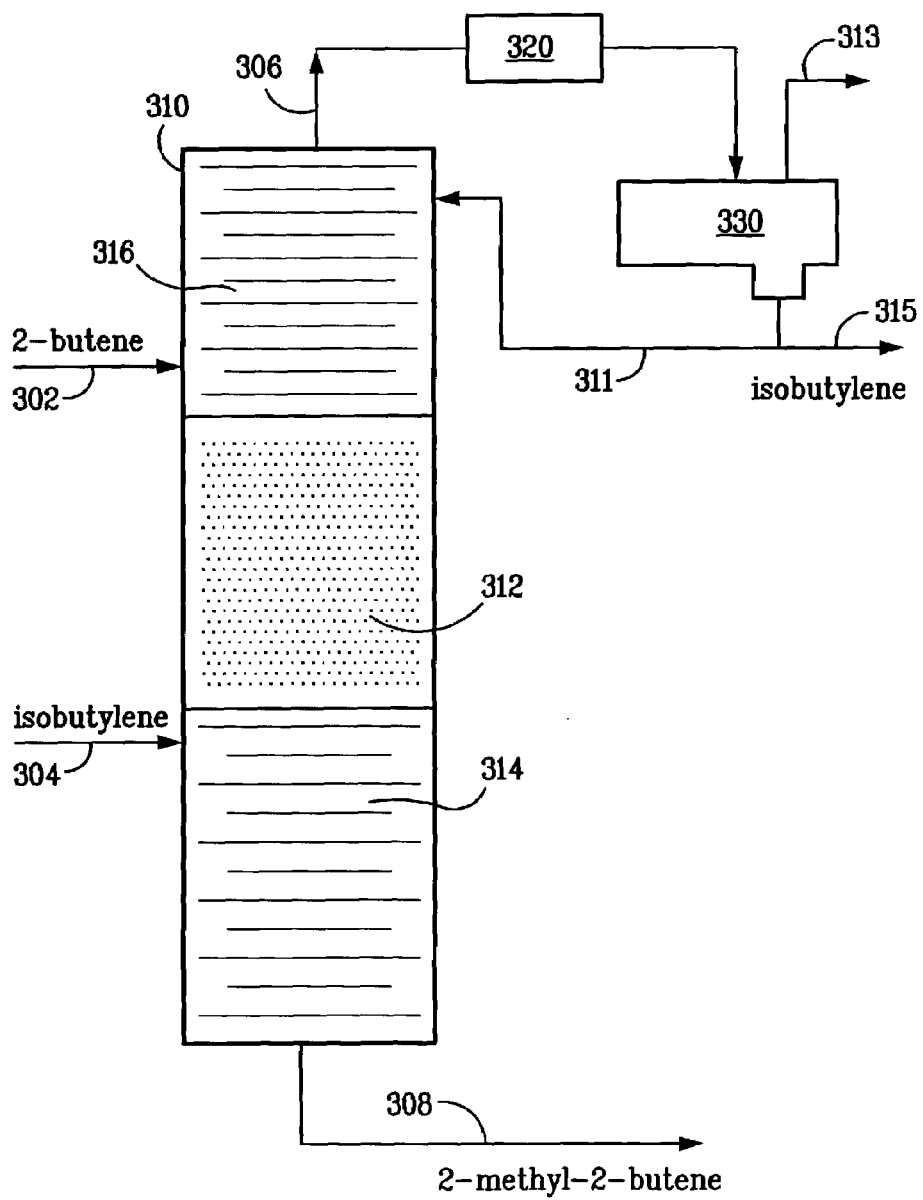
FIG. 3 is a schematic flow diagram of an embodiment for the production of 2-methyl-2-butene and propylene.

Referring now to FIG. 3 a simplified flow diagram of the process may be seen. The reaction distillation column 310 is seen to contain a bed 312 of the catalyst in the upper portion of the column. Below the catalyst bed 312 is a stripping section 314 containing standard distillation structure such as sieve trays, bubble cap trays or inert packing. Above the catalyst bed 312 is a rectification section 316 also containing standard distillation structure.

The isobutylene feed is fed into the catalyst bed 312 in liquid form via flow line 304. Unreacted isobutylene and product propylene are removed as overheads via flow line 306. The isobutylene is condensed in partial condenser 320 and collected and separated from the propylene in receiver 330. The liquid isobutylene may be returned to the distillation column 310 as reflux via flow line 311 or removed via flow line 315. Uncondensed materials are removed via flow line 313. The product 2-methyl-2-butene is recovered as bottoms via flow line 308. The 2-butene is refluxed internally within the distillation column reactor 310.

IV. TME/Neohexene Process

The metathesis of isobutylene with itself and the metathesis of diisobutylene with ethylene are both reversible in fixed bed reactors for a given residence time and may be written as follows:

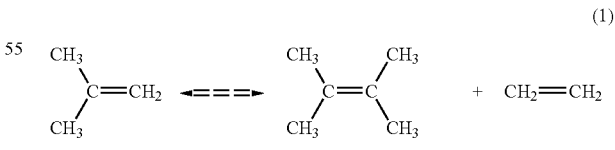

isobutylene tetramethylethylene (TME) ethylene

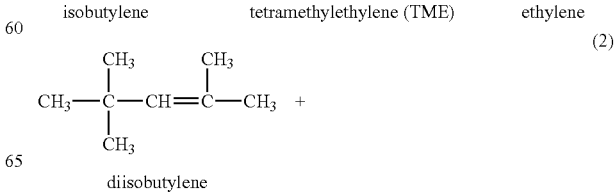

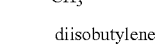

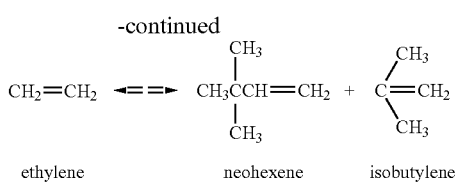

The two reactions are mutually supportive. Especially when it is considered that the isobutylene can oligomerize in the first reaction to form diisobutylene (not shown) which is useful in the second and the isobutylene produced in the second can be used in the first. Also the ethylene produced in the first can be used in the second.

The metathesis of isobutene to TME (1) is ideally suited to being carried out in a distillation column reactor. By adjusting the throughput, the product distribution and degree of conversion to TME and the degree of diisobutene oligomerization can be controlled.

The metathesis of diisobutylene and ethylene (2) is anticipated to be carried out in a standard fixed bed single pass reactor utilizing the same or similar catalyst as used in the first reaction. However, if practicable the use of a second distillation column reactor is included in the scope of the invention.

Figure 4:
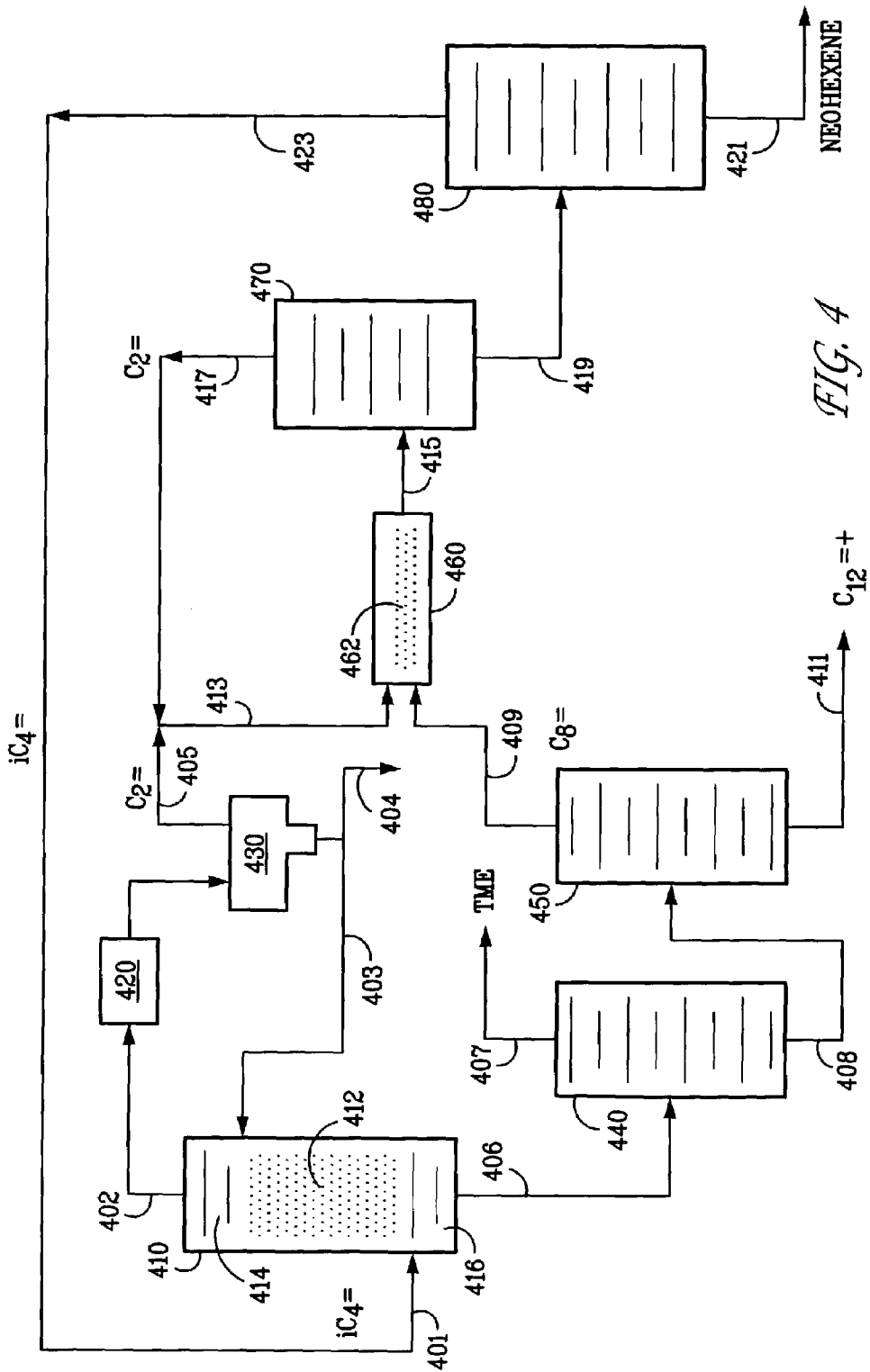
FIG. 4 is a schematic flow diagram of an embodiment for the production of TME and neohexene.

Referring now to the FIG. 4 a simplified flow diagram of the combined TME/neohexene process may be seen. The reaction distillation column 410 is seen to contain a bed 412 of the catalyst in the upper portion of the column. Below the catalyst bed 412 is a stripping section 416 containing standard distillation structure such as sieve trays, bubble cap trays or inert packing. Above the catalyst bed 412 is a rectification section 414 also containing standard distillation structure.

The isobutylene feed is fed into the catalyst bed 412 in liquid form via flow line 401. Unreacted isobutylene and product ethylene are removed as overheads via flow line 402. The isobutylene is condensed in partial condenser and collected and separated from the ethylene in receiver 430. The liquid isobutylene may be returned to the distillation column 410 as reflux via flow line 403 or removed via flow line 404. The product TME along with any oligomers are removed as bottoms via flow line 406.

The bottoms in flow line 406 are fed to a distillation column 440 where the product TME is separated as overheads via flow line 407 from the heavy oligomers which are taken as bottoms via flow line 408. The oligomers are further separated in distillation column 450 where the diisobutylene is taken as overheads. The $C_{12}=+$ oligomers are removed as bottoms via flow line 411.

The diisobutylene in flow line 409 is fed to reactor 460 which contains a fixed bed 462 of metathesis catalyst. A dryer (not shown) may be necessary to remove water in the overheads (line 405) before entry into reactor 460. The ethylene in flow line 405 from the receiver 430 is combined with recycle ethylene from flow line 417 and fed to reactor 460 via flow line 413. In reactor 460 the diisobutylene reacts with ethylene to produce neohexene and isobutylene. The effluent from the reactor in flow line 415 is fed to distillation column 470 where unreacted ethylene is separated as overheads via flow line 417 from the product neohexene and isobutylene which are taken as bottoms via flow line 419. The bottoms in flow line 419 are fed to another distillation column 480 wherein the product neohexene is separated from the isobutylene. The isobutylene is taken as overheads via flow 423 and recycled back to the distillation column reactor 410. Product neohexene is taken as bottoms via flow line 421.

Figure 5:
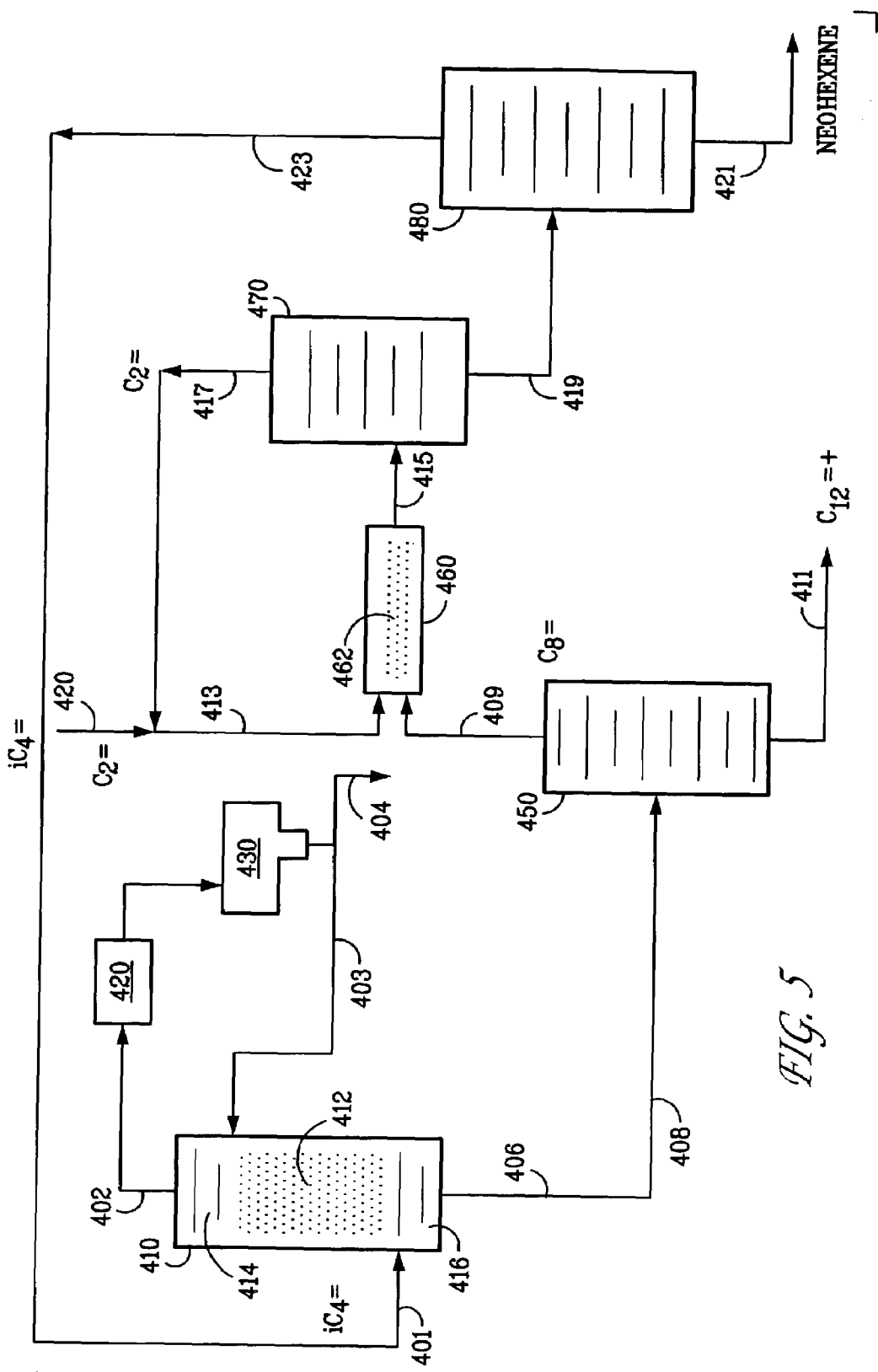
FIG. 5 is a schematic flow diagram of an embodiment for the production of neohexene.

In FIG. 5 the neohexene process alone is shown. The process is the same as that for the TME/neohexene process, except that the column 410 is operated to maximize diisobutene production as shown in U.S. Pat. No. 4,242,530, which is incorporated herein, column 440 is eliminated and the bottoms from the CD column go directly to splitter 450. The overhead 402 comprises unreacted isobutylene, other $C_4$'s and lower boiling components in minor amounts. Make up ethylene for the metathesis is supplied through line 420. The catalyst bed 412 comprises an acidic cation resin as described in the patent.

The invention claimed is:
1. An integrated process for the production of tetramethylethylene and neohexene comprising the steps of:
   (a) feeding isobutylene to a distillation column reactor containing a first fixed bed of metathesis catalyst prepared in the form of a catalytic distillation structure:
   (b) concurrently in said distillation column reactor
      (i) contacting said isobutylene with said first fixed bed metathesis catalyst so as to react at least a portion of said isobutylene to produce tetramethylethylene, ethylene, diisobutylene and heavier oligomers and create a reaction mixture containing unreacted isobutylene, ethylene, diisobutylene, heavier oligomers and tetramethylethylene product, and
      (ii) separating the ethylene and unreacted isobutylene from the tetramethylethylene, diisobutylene and heavier oligomers by fractional distillation;
   (c) removing the ethylene and isobutylene from said distillation column reactor as a first overheads product;
   (d) removing the tetramethylethylene product, diisobutylene and heavier oligomers from said distillation column reactor as a first bottoms;
   (e) separating said tetramethylethylene from said diisobutylene and heavier oligomers by fractional distillation wherein said tetramethylethylene is removed as a second overheads and said diisobutylene and heavier oligomers are removed as a second bottoms;
   (f) separating said diisobutylene from said heavier oligomers by fractional distillation; and
   (g) reacting at least a portion of said diisobutylene with at least a portion of the ethylene from said distillation column reactor in a reactor containing a second fixed bed of metathesis catalyst to produce neohexene and isobutylene.
2. The process according to claim 1 wherein the isobutylene is separated from said neohexene by fractional distillation and the separated isobutylene is recycled to said distillation column reactor as feed.

* * * * *